United States Patent
Palasis et al.

(10) Patent No.: US 7,402,155 B2
(45) Date of Patent: Jul. 22, 2008

(54) INJECTION APPARATUS FOR DELIVERING THERAPEUTIC

(75) Inventors: Maria Palasis, Wellesley, MA (US); Arthur Rosenthal, Boston, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 876 days.

(21) Appl. No.: 10/079,505

(22) Filed: Feb. 22, 2002

(65) Prior Publication Data

US 2002/0095124 A1   Jul. 18, 2002

Related U.S. Application Data

(63) Continuation of application No. 09/457,193, filed on Dec. 8, 1999, now Pat. No. 6,613,026.

(51) Int. Cl.
*A61M 5/32* (2006.01)
(52) U.S. Cl. .................... 604/272; 604/264
(58) Field of Classification Search ........... 604/164.01, 604/164.02, 164.03, 164.04, 164.06, 164.11, 604/171, 173, 176, 523, 264, 272; 606/167, 606/170
See application file for complete search history.

(56) References Cited

U.S. PATENT DOCUMENTS

| | | | | |
|---|---|---|---|---|
| 1,934,046 A * | 11/1933 | Demarchi | ........ | 604/115 |
| 3,817,248 A * | 6/1974 | Buckles et al. | ........ | 424/430 |
| 4,403,609 A * | 9/1983 | Cohen | ........ | 604/70 |
| 4,578,061 A | 3/1986 | Lemelson | ........ | 604/164 |
| 4,596,556 A | 6/1986 | Morrow et al. | ........ | 604/70 |
| 4,790,824 A | 12/1988 | Morrow et al. | ........ | 604/143 |
| 5,064,413 A | 11/1991 | McKinnon et al. | ........ | 604/70 |
| 5,098,389 A | 3/1992 | Cappucci | ........ | 604/158 |
| 5,236,424 A | 8/1993 | Imran | ........ | 604/280 |
| 5,262,128 A | 11/1993 | Leighton et al. | ........ | 422/100 |
| 5,324,276 A | 6/1994 | Rosenberg | ........ | 604/269 |
| 5,383,851 A | 1/1995 | McKinnon, Jr. et al. | ........ | 604/68 |
| 5,399,163 A | 3/1995 | Peterson et al. | ........ | 604/68 |

(Continued)

FOREIGN PATENT DOCUMENTS

CA   2241615 A1   12/1998

(Continued)

OTHER PUBLICATIONS

John Toon Internet Article, Georgia Tech Research News, "Taking The "Ouch" Out Of Needles: Arrays Of Micron-Scale "Microneedles" Offer New Technique For Drug Delivery" Released Jun. 22, 1998.

(Continued)

*Primary Examiner*—Manuel Mendez
(74) *Attorney, Agent, or Firm*—Kenyon & Kenyon LLP (57) ABSTRACT

A catheter for delivering therapeutic to an injection site within the body is provided. This catheter can include a shaft having a proximal end, a distal end, and an infusion lumen extending therein; a penetrating member coupled to the shaft and extendable from the distal end of the shaft, and a stabilizer positioned towards the distal end of the shaft. The catheter could also include a delivery system, able to be calibrated to deliver therapeutic through an injection port at a rate less than the therapeutic absorption rate of the injection site.

20 Claims, 4 Drawing Sheets

U.S. PATENT DOCUMENTS

| | | | | |
|---|---|---|---|---|
| 5,419,777 | A | 5/1995 | Hofling | 604/264 |
| 5,457,041 | A | 10/1995 | Ginaven et al. | 435/172.1 |
| 5,464,395 | A * | 11/1995 | Faxon et al. | 304/103.02 |
| 5,472,441 | A | 12/1995 | Edwards et al. | 606/41 |
| 5,478,328 | A | 12/1995 | Silverman et al. | 604/272 |
| 5,492,119 | A * | 2/1996 | Abrams | 600/375 |
| 5,509,900 | A * | 4/1996 | Kirkman | 604/104 |
| 5,520,639 | A | 5/1996 | Peterson et al. | 604/68 |
| 5,538,504 | A | 7/1996 | Linden et al. | 604/53 |
| 5,588,960 | A * | 12/1996 | Edwards et al. | 604/20 |
| 5,693,029 | A | 12/1997 | Leonhardt | 604/264 |
| 5,697,901 | A | 12/1997 | Eriksson | 604/46 |
| 5,702,384 | A | 12/1997 | Umeyama et al. | 604/892.1 |
| 5,735,847 | A * | 4/1998 | Gough et al. | 606/41 |
| 5,766,164 | A | 6/1998 | Mueller et al. | 606/15 |
| 5,782,823 | A | 7/1998 | Mueller | 606/7 |
| 5,807,395 | A | 9/1998 | Mulier et al. | 606/41 |
| 5,840,061 | A | 11/1998 | Menne et al. | 604/68 |
| 5,843,017 | A | 12/1998 | Yoon | 604/22 |
| 5,899,915 | A * | 5/1999 | Saadat | 606/170 |
| 5,997,525 | A | 12/1999 | March et al. | 604/508 |
| 6,152,918 | A * | 11/2000 | Padilla et al. | 606/15 |
| 6,203,556 | B1 | 3/2001 | Evans et al. | 606/185 |
| 6,217,554 | B1 | 4/2001 | Green | 604/164.01 |
| 6,302,870 | B1 * | 10/2001 | Jacobsen et al. | 604/272 |
| 6,626,902 | B1 * | 9/2003 | Kucharczyk et al. | 606/41 |

FOREIGN PATENT DOCUMENTS

| | | |
|---|---|---|
| EP | 196 07 922 A1 | 8/1999 |
| WO | WO 92/10142 A1 | 6/1992 |
| WO | WO 98/05307 A1 | 2/1998 |
| WO | WO 99/04851 | 2/1999 |
| WO | WO 99/39624 A1 | 8/1999 |
| WO | WO 99/44524 A2 | 9/1999 |
| WO | WO 99/48545 A1 | 9/1999 |
| WO | WO 99/49926 | 10/1999 |

OTHER PUBLICATIONS

Source Unknown "Chemical Engineers Develop Microneedles for Painfree Injections," Dec. 1998, one page.

* cited by examiner

INJECTION APPARATUS FOR DELIVERING THERAPEUTIC

RELATED APPLICATIONS

This application is a continuation of patent application Ser. No. 09/457,193 filed Dec. 8, 1999 now U.S. Pat. No. 6,613,026, entitled LATERAL NEEDLE-LESS INJECTION APPARATUS AND METHOD.

FIELD OF THE INVENTION

The present invention generally relates to delivering and injecting fluid into heart tissue. More specifically, the present invention relates to delivering and injecting fluid into heart tissue utilizing laterally directed injection ports.

BACKGROUND OF THE INVENTION

Injection catheters may be used to inject therapeutic or diagnostic agents into a variety of organs, such as the heart. In the case of injecting a therapeutic agent into the heart, 27 or 28 gauge needles are generally used to inject solutions carrying genes, proteins, or drugs directly into the myocardium. A typical volume of an agent delivered to an injection site is about 100 microliters. A limitation to this method of delivering therapeutic agents to the heart is that the injected fluid tends to leak from the site of the injection after the needle is disengaged from the heart. In fact, fluid may continue to leak over several seconds. In the case of dynamic organs such as the heart, there may be more pronounced leakage with each muscle contraction.

Therapeutic and diagnostic agents may be delivered to a portion of the heart as part of a percutaneous myocardial revascularization (PMR) procedure. PMR is a procedure which is aimed at assuring that the heart is properly oxygenated. Assuring that the heart muscle is adequately supplied with oxygen is critical to sustaining the life of a patient. To receive an adequate supply of oxygen, the heart muscle must be well perfused with blood. In a healthy heart, blood perfusion is accomplished with a system of blood vessels and capillaries. However, it is common for the blood vessels to become occluded (blocked) or stenotic (narrowed). A stenosis may be formed by an atheroma which is typically a harder, calcified substance which forms on the walls of a blood vessel.

Historically, individual stenotic lesions have been treated with a number of medical procedures including coronary bypass surgery, angioplasty, and atherectomy. Coronary bypass surgery typically involves utilizing vascular tissue from another part of the patient's body to construct a shunt around the obstructed vessel. Angioplasty techniques such as percutaneous transluminal angioplasty (PTA) and percutaneous transluminal coronary angioplasty (PTCA) are relatively non-invasive methods of treating a stenotic lesion. These angioplasty techniques typically involve the use of a guide wire and a balloon catheter. In these procedures, a balloon catheter is advanced over a guide wire such that the balloon is positioned proximate a restriction in a diseased vessel. The balloon is then inflated and the restriction in the vessel is opened. A third technique which may be used to treat a stenotic lesion is atherectomy. During an atherectomy procedure, the stenotic lesion is mechanically cut or abraded away from the blood vessel wall.

Coronary by-pass, angioplasty, and atherectomy procedures, have all been found effective in treating individual stenotic lesions in relatively large blood vessels. However, the heart muscle is perfused with blood through a network of small vessels and capillaries. In some cases, a large number of stenotic lesions may occur in a large number of locations throughout this network of small blood vessels and capillaries. This tortuous path and small diameter of these blood vessels limit access to the stenotic lesions. The sheer number and small size of these stenotic lesions make techniques such as cardiovascular by-pass surgery, angioplasty, and atherectomy impractical.

When techniques which treat individual lesion are not practical, percutaneous myocardial revascularization (PMR) may be used to improve the oxygenation of the myocardial tissue. A PMR procedure generally involves the creation of holes, craters or channels directly into the myocardium of the heart. In a typical PMR procedure, these holes are created using radio frequency energy delivered by a catheter having one or more electrodes near its distal end. After the wound has been created, therapeutic agents are sometimes ejected into the heart chamber from the distal end of a catheter.

Positive clinical results have been demonstrated in human patients receiving PMR treatments. These results are believed to be caused in part by blood flowing within the heart chamber through channels in myocardial tissue formed by PMR. Increased blood flow to the myocardium is also believed to be caused in part by the healing response to wound formation. Specifically, the formation of new blood vessels is believed to occur in response to the newly created wound. This response is sometimes referred to as angiogenesis. After the wound has been created, therapeutic agents which are intended to promote angiogenesis are sometimes injected into the heart chamber. A limitation of this procedure is that the therapeutic agent may be quickly carried away by the flow of blood through the heart.

In addition to promoting increased blood flow, it is also believed that PMR improves a patient's condition through denervation. Denervation is the elimination of nerves. The creation of wounds during a PMR procedure results in the elimination of nerve endings which were previously sending pain signals to the brain as a result of hibernating tissue.

Currently available injection catheters are not particularly suitable for accurately delivering small volumes of therapeutic agents to heart tissue. Improved devices and methods are desired to address the problems associated with retention of the agent in the heart tissue as discussed above. This is particularly true for agents carrying genes, proteins, or other angiogenic drugs which may be very expensive, even in small doses.

SUMMARY OF THE INVENTION

The present invention regards devices for delivering therapeutic within the body. A catheter embodying the invention includes a shaft having a proximal end, a distal end, and an infusion lumen extending therein; a penetrating member coupled to the shaft and extendable from the distal end of the shaft, the penetrating member having an injection port and a piercing tip; and a stabilizer positioned towards the distal end of the shaft. A second catheter embodying the invention includes a shaft having a proximal end, a distal end, and an infusion lumen extending therein; a penetrating member coupled to the shaft and extendable from the distal end of the shaft, the penetrating member having an injection port and a piercing tip; and a delivery system, the delivery system able to be calibrated to deliver therapeutic through the injection port at a rate less than the therapeutic absorrnion rate of the injection site.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1A:
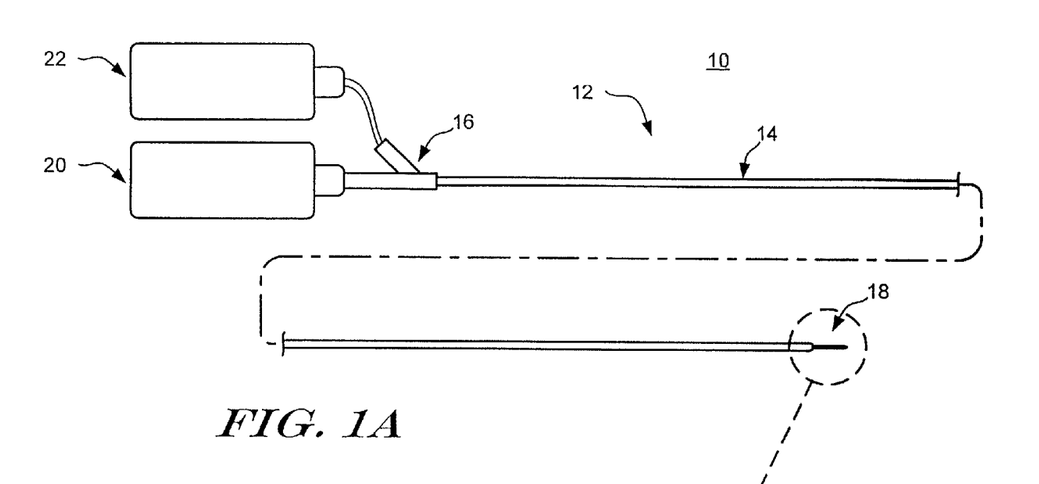
FIG. 1A is a plan view of a catheter system in accordance with an exemplary embodiment of the present invention.

Refer now to FIG. 1A which illustrates a plan view of a catheter system 10 in accordance with an exemplary embodiment of the present invention. Catheter system 10 includes a catheter 12 having an elongate shaft 14. A manifold 16 is connected to the proximal end of the elongate shaft 14. The elongate shaft 14 includes a distal portion 18 which is illustrated in greater detail in FIG. 1B.

A pressurized fluid source 20 is connected to the catheter 12 by way of the manifold 16. Optionally, a vacuum source may be coupled to the side arm of the manifold 16. The pressurized fluid source 20 may comprise a conventional syringe or an automated pressure source such as a high pressure injection system. An example of a high pressure injection system is disclosed in U.S. Pat. No. 5,520,639 to Peterson et al. which is hereby incorporated by reference. The system may be gas driven, such as with carbon dioxide, or it may be mechanically driven, with a spring, for example, to propel the solution. Similarly, vacuum source 22 may comprise a conventional syringe or other suitable vacuum means such as a vacuum bottle.

Figure 1B:
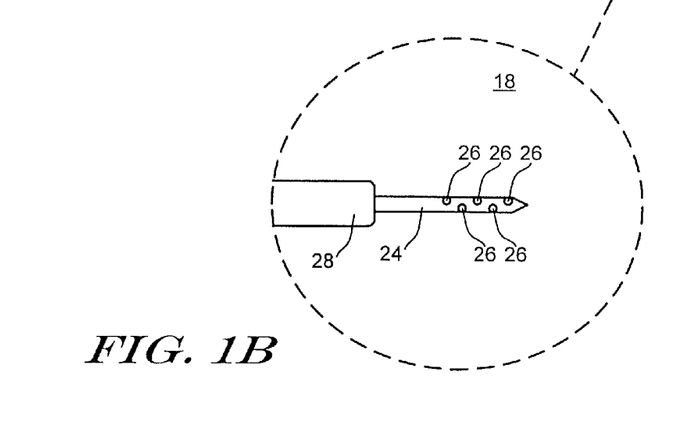
FIG. 1B is an enlarged detailed view of the distal end of the catheter illustrated in FIG. 1A.

Refer now to FIG. 1B which illustrates an enlarged detailed view of the distal portion 18 of the elongate shaft 14. The distal portion 18 of the elongate shaft 14 includes a penetrating member 24 coaxially disposed in an elongate outer sheath 28. The penetrating member 24 contains a plurality of injection ports 26 disposed adjacent the distal end thereof. The injection ports 26 are in fluid communication with the pressurized fluid source 20 via penetrating member 24 and manifold 16.

Figure 2:
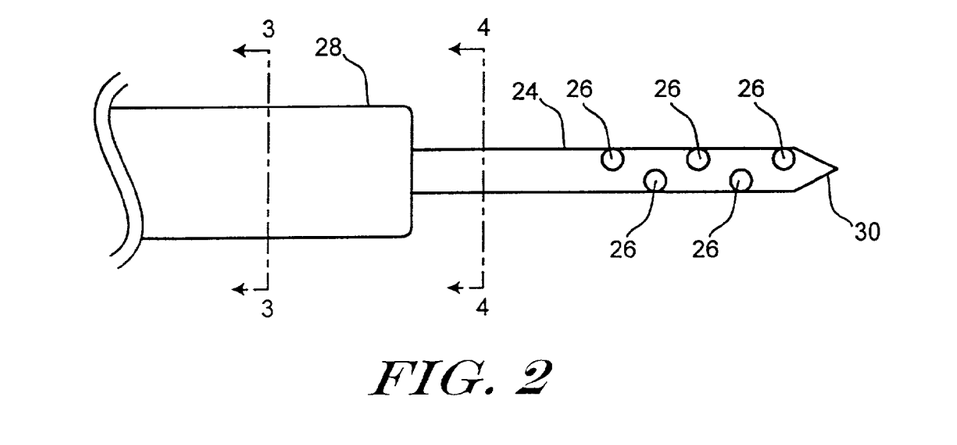
FIG. 2 is a further enlarged view of the distal end of the catheter illustrated in FIG. 1A.

With reference to FIG. 2, the penetrating member 24 includes a sharpened distal end 30 to facilitate easy penetration of tissue. The injection ports 26 extend through the wall of the penetrating member 24. The injection ports 26 each have an axis that is at an angle with the longitudinal axis of the penetrating member 24. The axis of each injection port 26 may be orthogonal to the axis of the penetrating member 24 or any other desired angle. The angle of the axis of each injection port 26 determines in part the penetration angle of the fluid as discussed in greater detail with reference to FIGS. 6A-6C.

Figure 3:
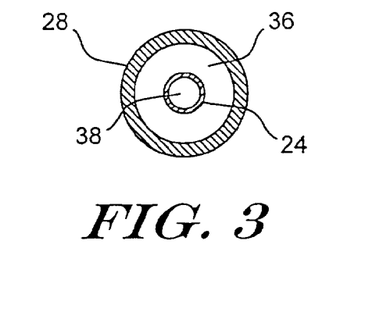
FIG. 3 is a lateral cross-sectional view taken along line 3-3 in FIG. 2.
Figure 7A:
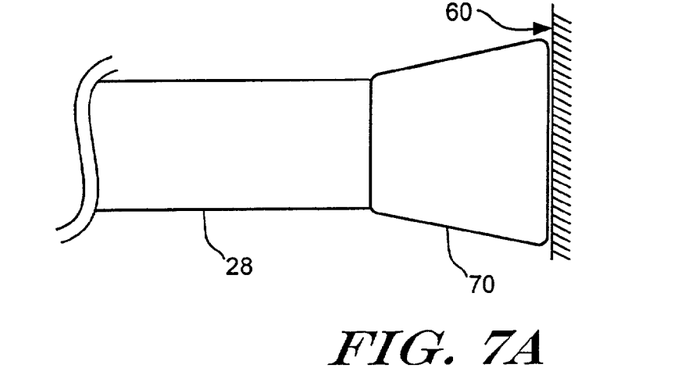
FIGS. 7A-7C illustrate a sequence of steps for using an alternative embodiment of the system illustrated in FIG. 1A, incorporating a stabilizing suction head.
Figure 7B:
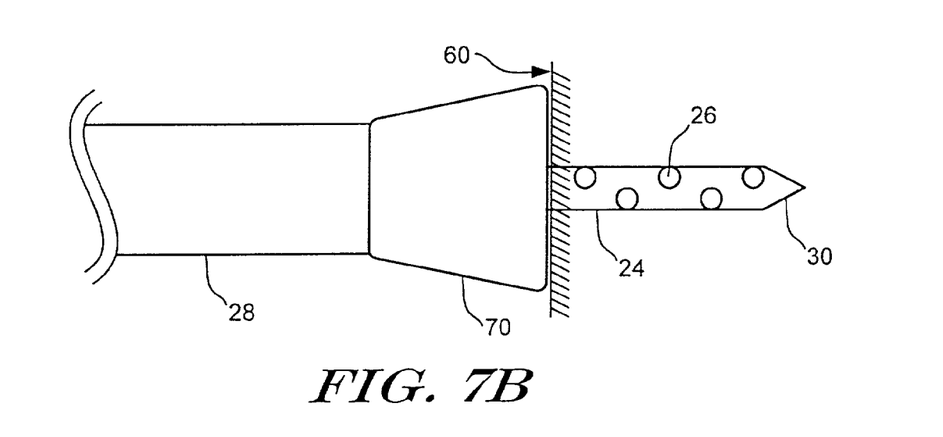
Figure 7C:
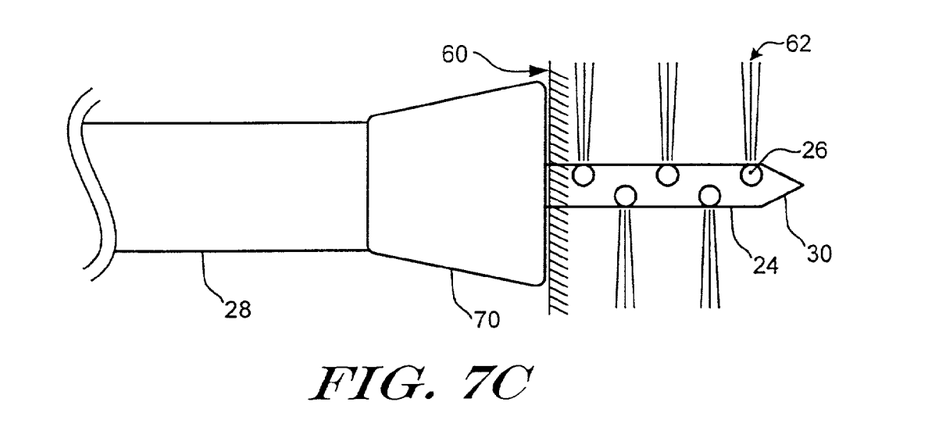

With reference to FIG. 3, a lateral cross-sectional view taken along line 3-3 in FIG. 2 is shown. The shaft 14 includes an annular lumen 36 defined between the interior of the sheath 28 and the exterior of the penetrating member 24. The annular lumen 36 may be used to infuse fluids for purposes of fluoroscopic visualization and/or aspiration. Alternatively, the annular lumen 36 may be used to facilitate the application of suction for stabilization purposes as will be discussed in greater detail with reference to FIGS. 7A-7C.

The elongate shaft 14 has characteristics (length, profile, flexibility, pushability, trackability, etc.) suitable for navigation from a remote access site to the treatment site within the human body. For example, the elongate shaft 14 may have characteristics suitable for intravascular navigation to the coronary tissue from a remote access site in the femoral artery. Alternatively, the elongate shaft 14 may have characteristics suitable for transthoracic navigation to the coronary tissue from a remote access point in the upper thorax. Those skilled in the art will recognize that the shaft 14 may have a wide variety of dimensions, materials, constructions, etc. depending on the particular anatomy being traversed.

Figure 4:
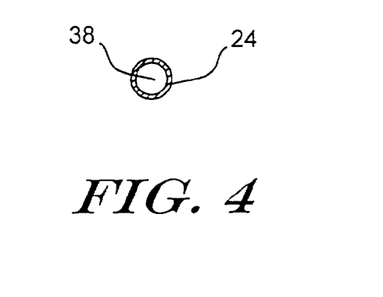
FIG. 4 is a lateral cross-sectional view taken along line 4-4 in FIG. 2.
Figure 5:
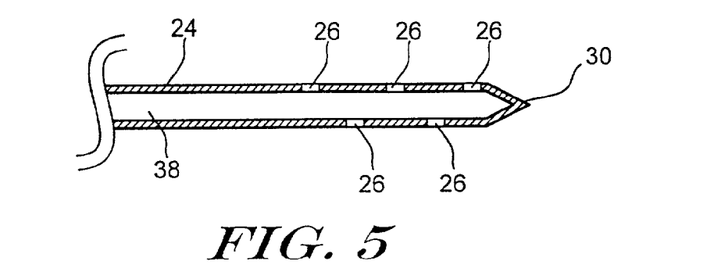
FIG. 5 is a simplified longitudinal cross-sectional view of the penetrating member.

Refer now to FIG. 4 which illustrates a lateral cross-sectional view taken along line 4-4 in FIG. 2. Penetrating member 24 includes an internal lumen 38 in fluid communication with the injection ports 26. The injection ports 26 are in fluid communication with the pressurized fluid source 20 via lumen 38 of penetrating member 24 such that fluid may be readily delivered from the pressurized fluid source 20 through the shaft 14 and into the heart tissue being treated. Fluid communication between the pressurized fluid source 20 and the injection ports 26 may be defined by a direct connection between the proximal end of the penetrating member 24 and the source 20 via manifold 16. Such fluid communication may also be defined in part by an intermediate tube connected to the proximal end of the penetrating member 24.

The penetrating member 24 may have a length slightly greater than the length of the outer sheath 28, with a penetrating length of approximately 1 to 10 mm. The inside diameter of the penetrating member 24 should be sufficiently large to accommodate the desired flow rate of fluid, but sufficiently small to reduce the amount of fluid waste remaining in the lumen 38 after the procedure is complete. For example, the penetrating member 24 may have an inside diameter in the range of 1 to 250 microns and an outside diameter in the range of 10 microns to 1.25 mm. The penetrating member 24 may be formed of stainless steel or other suitable material such as nickel titanium alloy. The injection ports 26 may have a diameter ranging from approximately 1 to 500 microns.

Figure 6A:
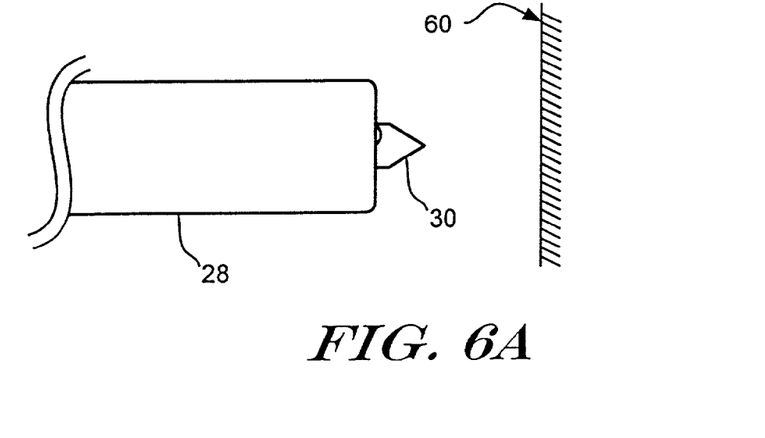
FIGS. 6A-6C illustrate a sequence of steps for using the system illustrated in FIG. 1A.
Figure 6B:
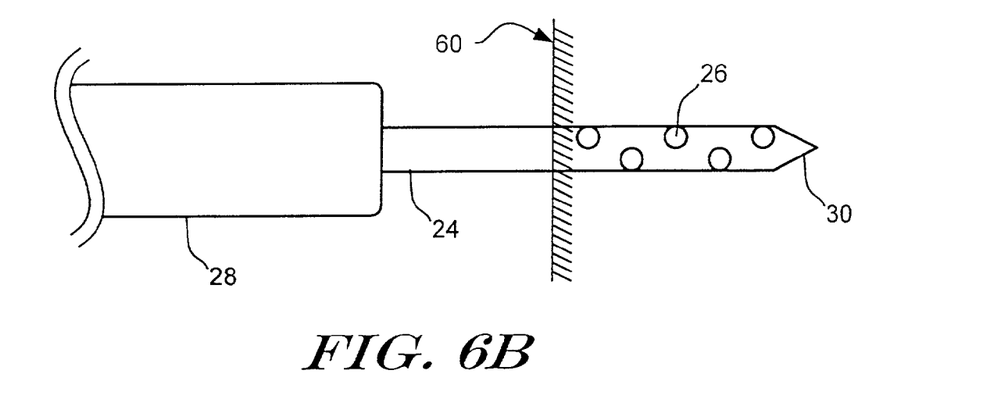
Figure 6C:
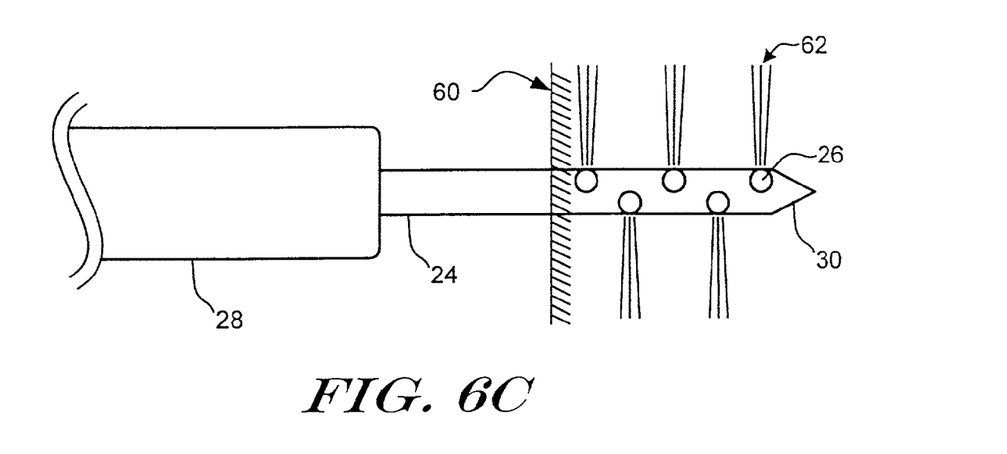

Refer now to FIGS. 6A-6C which illustrate operation of the catheter system 10. The heart tissue 60 (i.e., myocardium) may be accessed from the interior of the heart by, for example, navigating the catheter 12 through the vascular system into a chamber of the heart. Alternatively, the heart tissue 60 may be accessed from the exterior of the heart by, for example, transthoracic minimally invasive surgery in which the catheter 12 is navigated through the upper thoracic cavity adjacent the epicardium of the heart.

Regardless of the approach, the distal portion 18 of the catheter 12 is positioned adjacent the desired treatment site of the heart tissue 60 utilizing conventional visualization techniques such as x-ray, fluoroscopy or endoscopic visualization. While positioning the catheter 12, the penetrating member 24 may be partially retracted in the outer sheath 28 such that only the distal end 30 of the penetrating member 24 is exposed, or fully retracted such that the entire penetrating member 24 is contained within the outer sheath 28.

With the distal portion 18 positioned adjacent the heart tissue 60 as shown in FIG. 6A, the penetrating member 24 is advanced into the heart tissue 60 until the distal end 30 of the penetrating member 24 reaches a sufficient depth to position the injection ports 26 completely within the tissue 60 as shown in FIG. 6B. This position may be confirmed by injecting radiopaque contrast media or colored dye through the inner lumen 38 of the penetrating member 24 such that the contrast media or dye exits the injection ports 26.

Once in position, fluid 62 may be infused from the pressurized fluid source 20 through the lumen 38 of the penetrating member and through the injection ports 26 and into the heart tissue 60. After the fluid 62 has been delivered via the injection lumens in the injection ports 26, the penetrating member 24 may be retracted into the outer sheath 28. After retraction, the entire catheter 12 may be removed from the patient.

The pressure applied by the pressurized fluid source 20 to deliver the fluid 62 into the heart tissue 60 may vary depending on the desired result. For example, a relatively low pressure of approximately 0.01 to 1 ATM may be utilized to deliver the fluid 62 into the heart tissue 60 thereby minimizing trauma to the tissue adjacent the injection site. Alternatively, a relatively high pressure of approximately 10 to 300 ATM may be utilized to increase the depth penetration of the fluid 62 into the heart tissue 60 and/or to dispense the solution throughout the injected tissue.

The penetration depth of the fluid 62 into the tissue 60 influences fluid retention, the volume of tissue 60 treated and the degree of trauma to the tissue 60. The penetration depth of the fluid 62 is dictated, in part, by the exit velocity of the fluid 62, the size of the fluid stream 62, and the properties of the tissue 60. The exit velocity, in turn, depends on the applied pressure of the pressurized fluid source 20, the drag or pressure drop along the length of the lumen 38 and the ports 26, and the cross-sectional area or size of the ports 26. The size of the fluid stream 62 also depends on the size of the ports 26. Thus, assuming the treatment site dictates the tissue 60 properties, the penetration depth may be selected by adjusting the applied pressure of the pressurized fluid source 20, the size and length of the lumen 38, and the cross-sectional area of the ports 26. By adjusting these parameters, fluid retention, treated tissue volume and degree of trauma may be modified as required for the particular clinical application.

As can be appreciated from the illustration of FIG. 6C, by injecting the fluid 62 in a direction different from the direction of penetration of the penetrating member 24, the fluid 62 will be retained within the heart tissue 60. Retention of the fluid 62 in the heart tissue 60 is primarily accomplished by forming the injection ports at an angle relative to the direction of penetration of the penetrating member 24, i.e., the longitudinal axis of the penetrating member 24. In addition to providing better retention of the fluid 62 within the heart tissue 60, this arrangement also allows for a greater volume of heart tissue 60 to be treated with a single primary penetration.

In an embodiment of the present invention, a low volume (several microliters but less than 100 microliters by a single injection) of solution is delivered to the heart such that it may absorb the delivered solution within the time frame of the injection. In contrast to higher volume injections, the heart is more capable of absorbing these low volumes. The effect of the low volume injection is to minimize expulsion by the tissue. In order to deliver the entire dose of virus, it may be desirable or necessary to concentrate the injection (i.e., deliver the same number of viral particles or micrograms of protein, typically delivered in 100 µl, in a volume of 10 µl) or keep the concentration of virus the same as that typically used, but increase the number of injections from 10 (typical) to 20, 30, or more.

Each injectate may also be delivered in a prolonged manner such that the heart can absorb the solution as it is being injected (rate of delivery $<$rate of tissue absorption). For instance, the injection can be delivered at a defined flow rate using a syringe pump. The time of injection will depend on the volume to be delivered. For example, low volumes (a few microliters) may be delivered in under a minute while higher volumes (10 to 100 μl or more) may be delivered over several minutes. In this instance, it may be beneficial to include a method which gently attaches the injection catheter to the wall of the heart, for instance suction or vacuum.

Thus, to accomplish this result, the injection ports 26 may be formed at an angle to the longitudinal axis of the penetrating member 24. Preferably, the axes of the injection ports 26 are generally lateral to the longitudinal axis of the penetrating member 24. However, the axes of the injection ports 26 may be formed at an angle of about 5 to about 90 degrees relative to the axis of the penetrating member 24 to accomplish essentially the same result. Also preferably, the penetrating member 24 penetrates the heart tissue 60 in a direction generally orthogonal to the surface of the heart tissue 60 adjacent the injection site.

Refer now to FIGS. 7A-7C which illustrate operation of an alternative embodiment of the catheter system 10. In this particular embodiment, the distal portion of the catheter 12 incorporates a suction head 70 connected to the distal head of the outer sheath 28. The suction head 70 comprises a flexible tubular member having a generally conical shape. The suction head 70 has an interior which is in fluid communication with the inner lumen 36 of the outer sheath 28. As mentioned previously, the inner lumen 36 of the outer sheath 28 is in fluid communication with the vacuum source 22. By actuating the vacuum source 22, suction is applied to the suction head via the inner lumen 36 of the outer sheath 28.

The suction head is positioned adjacent the heart tissue 60 as illustrated in FIG. 7A. The suction head 70 grasps the surface of the heart tissue 60 thereby stabilizing the distal portion 18 of the catheter 12. This is particularly beneficial when treating tissue in a dynamic setting such as when the heart is beating. Absent a stabilizing means such as suction head 70, it maybe difficult to maintain the distal portion 18 in a relatively fixed position if the treatment site is not stationary. Those skilled in the art will recognize that other stabilizing means may be utilized such as removable screw anchors, miniature forceps, etc.

After suction is applied to the suction head 70 thereby stabilizing the distal portion 18 of the catheter 12, the penetrating member 24 is advanced into the heart tissue 60 as illustrated in FIG. 7B. Once the injection ports 26 of the penetrating member 24 are completely embedded within the heart tissue 60, fluid 62 may be delivered into the heart tissue 60 via the injection ports 26 as discussed previously.

After the fluid 62 has been delivered to the heart tissue 60, the penetrating member 24 may be retracted into the outer sheath 28. After retracting the penetrating member 24, the suction applied by the suction head 70 is terminated to release the distal portion 18 of the catheter from the heart tissue 60. The entire catheter system 12 may then be removed from the patient.

From the foregoing, it is apparent that the present invention provides a device and method for delivering and injecting fluid into heart tissue to improve delivery efficiency. This is accomplished by utilizing injection ports which direct fluid in a direction different from the direction of penetration of the penetrating member. Thus, fluid leakage from the injection site is reduced and the fluid is distributed over a greater volume of tissue.

Although treatment of the heart is used as an example herein, the medical devices of the present invention are useful for treating any mammalian tissue or organ. Nonlimiting examples include tumors; organs including but not limited to the heart, lung, brain, liver, kidney, bladder, urethra and ureters, eye, intestines, stomach, pancreas, ovary, prostate; skeletal muscle; smooth muscle; breast, cartilage and bone.

The terms "therapeutic agents" and "drugs" are used interchangeably herein and include pharmaceutically active compounds, cells, nucleic acids with and without carrier vectors such as lipids, compacting agents (such as histones), virus, polymers, proteins, and the like, with or without targeting sequences.

Specific examples of therapeutic agents used in conjuction with the present invention include, for example, proteins, oligonucleotides, ribozymes, anti-sense genes, DNA compacting agents, gene/vector systems (i.e., anything that allows for the uptake and expression of nucleic acids), nucleic acids (including, for example, recombinant nucleic acids; naked DNA, cDNA, RNA; genomic DNA, cDNA or RNA in a noninfectious vector or in a viral vector which may have attached peptide targeting sequences, antisense nucleic acid (RNA or DNA); and DNA chimeras which include gene sequences and encoding for ferry proteins such as membrane translocating sequences ("MTS") and herpes simplex virus-I ("VP22"), and viral, liposomes and cationic polymers that are selected from a number of types depending on the desired application. Other pharmaceutically active materials include anti-thrombogenic agents such as heparin, heparin derivatives, urokinase, and PPACK (dextrophenylalanine proline arginine chloromethylketone); antioxidants such as probucol and retinoic acid; angiogenic and anti-angiogenic agents; agents blocking smooth muscle cell proliferation such as rapamycin, angiopeptin, and monoclonal antibodies capable of blocking smooth muscle cell proliferation; anti-inflammatory agents such as dexamethasone, prednisolone, corticosterone, budesonide, estrogen, sulfasalazine, acetyl salicylic acid, and mesalamine; calcium entry blockers such as verapamil, diltiazem and nifedipine; antineoplastic/antiproliferative/anti-mitotic agents such as pad itaxel, 5-fluorou racil, methotrexate, doxorubicin, daunorubicin, cyclosporine, cisplatin, vinblastine, vincristine, epothilones, endostatin, angiostatin and thymidine kinase inhibitors; antimicrobials such as triclosan, cephalosporins, aminoglycosides, and nitrofurantoin; anesthetic agents such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, an RGD peptidecontaining compound, heparin, antithrombin compounds, platelet receptor antagonists, antithrombin antibodies, anti-platelet receptor antibodies, enoxaparin, hirudin, Warfarin sodium, Dicumarol, aspirin, prostaglandin inhibitors, platelet inhibitors and tick antiplatelet factors; vascular cell growth promotors such as growth factors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; agents which interfere with endogeneus vascoactive mechanisms; survival genes which protect against cell death, such as anti-apoptotic Bcl-2 family factors and Akt kinase; and combinations thereof.

Examples of polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic proteins or polypeptides. A polypeptide is understood to be any translation product of a polynucleotide regardless of size, and whether glycosylated or not. Therapeutic proteins and polypeptides include as a primary example, those proteins or polypeptides that can compensate for defective or deficient species in an animal, or those that act through toxic effects to limit or remove harmful cells from the body. In addition, the polypeptides or proteins useful in the present invention include, without limitation, angiogenic factors and other molecules competent to induce angiogenesis, including acidic and basic fibroblast growth factors, vascular endothelial growth factor, hif-1, epidermal growth factor, transforming growth factor $\alpha$ and $\beta$, platelet-derived endothelial growth factor, platelet-derived growth factor, tumor necrosis factor $\alpha$, hepatocyte growth factor and insulin like growth factor; growth factors; cell cycle inhibitors including CDK inhibitors; anti-restenosis agents, including p15, p16, p18, p19, p21, p27, p53, p57, Rb, nFkB and E2F decoys, thymidine kinase ("TK") and combinations thereof and other agents useful for interfering with cell proliferation, including agents for treating malignancies; and combinations thereof. Still other useful factors, which can be provided as polypeptides or as DNA encoding these polypeptides, include monocyte chemoattractant protein ("MCP-1"), and the family of bone morphogenic proteins ("BMPs"). The known proteins include BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMPs are any of BMP-2, BMP-3, BMP-4, BMP-5, BMP-6 and BMP-7. These dimeric proteins can be provided as homodimers, heterodimers, or combinations thereof, alone or together with other molecules. Alternatively or, in addition, molecules capable of inducing an upstream or downstream effect of a BMP can be provided. Such molecules include any of the "hedgehog" proteins, or the DNAs encoding them.

The present invention is also useful in delivering cells as the therapeutic agent. Cells can be of human origin (autologous or allogeneic) or from an animal source (xenogeneic), genetically engineered if desired to deliver proteins of interest at a delivery or transplant site. The delivery media is formulated as needed to maintain cell function and viability.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A catheter for delivering therapeutic to an injection site within the body, comprising:
    a shaft having a proximal end, a distal end, and an infusion lumen extending therein;
    a penetrating member coupled to the shaft and extendable from the distal end of the shaft, the penetrating member having an injection port and a piercing tip, wherein the penetrating member penetrates the injection site in a first direction, and wherein the injection port directs therapeutic in a second direction different from the first direction; and a stabilizer positioned towards the distal end of the shaft, wherein the stabilizer is adapted to maintain the distal end of the shaft against the injection site while the penetrating member penetrates the injection site.

2. The catheter of claim 1 wherein the stabilizer comprises a suction head.

3. The catheter of claim 2 wherein the suction head is coupled to a suction lumen.

4. The catheter of claim 1 further comprising:
a therapeutic delivery system, the system adjustable to deliver therapeutic through the injection port at various pre-selected pressure ranges.

5. The catheter of claim 4 wherein the delivery system includes a therapeutic vessel and wherein the delivery system is adjusted to deliver therapeutic through the injection port at a pressure of less than one atmosphere.

6. The catheter of claim 4 wherein the delivery system includes a therapeutic vessel and wherein the delivery system is adjusted to deliver therapeutic through the injection port at a pressure of greater than one atmosphere.

7. The catheter of claim 4 wherein the delivery system is adjusted to deliver therapeutic at a rate less than the therapeutic absorption rate of the injection site.

8. The catheter of claim 1 wherein said second direction is at an angle non-orthogonal and non-parallel to the first direction.

9. The catheter of claim 1 wherein the penetrating member has a plurality of injection ports that direct therapeutic in a direction different from the first direction.

10. A catheter for delivering therapeutic to an injection site within the body, comprising:
a shaft having a proximal end, a distal end, and an infusion lumen extending therein;
a penetrating member coupled to the shaft and extendable from the distal end of the shaft,
the penetrating member having an injection port and a piercing tip, wherein the penetrating member penetrates the injection site in a first direction, and wherein the injection port directs therapeutic in a second direction different from the first direction; and
a delivery system, the delivery system able to be calibrated to deliver therapeutic through the injection port at a rate less than the therapeutic absorption rate of the injection site.

11. The catheter of claim 10 further comprising:
a stabilizer positioned towards the distal end of the shaft.

12. The catheter of claim 11 wherein the stabilizer comprises a suction head.

13. The catheter of claim 12 wherein the suction head is coupled to a suction lumen.

14. The catheter of claim 11 wherein the stabilizer comprises a forceps.

15. The catheter of claim 11 wherein the stabilizer comprises a penetrating anchor.

16. The catheter of claim 10 wherein the delivery system includes a therapeutic vessel and wherein the delivery system is calibrated to deliver therapeutic through the injection port at a pressure of less than one atmosphere.

17. The catheter of claim 10 wherein the delivery system includes a therapeutic vessel and wherein the delivery system is calibrated to deliver therapeutic through the injection port at a pressure of greater than one atmosphere.

18. The catheter of claim 10 wherein said second direction is at an angle non-orthogonal and non-parallel to the first direction.

19. The catheter of claim 10 wherein the penetrating member has a plurality of injection ports that direct therapeutic in a direction different from the first direction.

20. A catheter injection system for delivering therapeutic to an injection site within the body, comprising:
a shaft having a proximal end, a distal end, and an infusion lumen extending therein;
a penetrating member coupled to the shaft and extendable from the distal end of the shaft, the penetrating member having an injection port and a piercing tip; and
a stabilizer for maintaining the distal end of the shaft in a relatively fixed position while the penetrating member penetrates the injection site;
wherein the penetrating member penetrates the injection site in a first direction, and wherein the injection port directs therapeutic in a second direction different from the first direction, said second direction is at an angle non-orthogonal and non-parallel to the first direction such that therapeutic leakage from the injection site is reduced.

* * * * *

UNITED STATES PATENT AND TRADEMARK OFFICE
CERTIFICATE OF CORRECTION

PATENT NO. : 7,402,155 B2
APPLICATION NO. : 10/079505
DATED : July 22, 2008
INVENTOR(S) : Palasis et al.

It is certified that error appears in the above-identified patent and that said Letters Patent is hereby corrected as shown below:

Column 2, line 66, "absorrnion" should be changed to --absorption--;
Column 6, line 6, "< rate" should be changed to --≤ rate--;
Column 6, line 44, "maybe" should be changed to --may be--;
Column 7, line 14, "virus," should be changed to --viruses,--;
Column 7, line 29, "("VP22")" should be changed to --("VP22"))--;
Column 7, line 29, "viral, liposomes" should be changed to --viral liposomes--;
Column 7, line 43, "pad itaxel, 5-fluorou racil," should be changed to --paclitaxel, 5-fluorouracil,--;
Column 7, line 50, "lisidomine" should be changed to --linsidomine--;
Column 7, line 53, "peptidecontaining" should be changed to --peptide-containing--;
Column 7, line 58, "promoters" should be changed to --promoters--;
Column 7, line 60, "promoters" should be changed to --promoters--; and
Column 8, line 1, "endogeneus vascoactive" should be changed to --endogenous vasoactive--.

Signed and Sealed this

Eighteenth Day of August, 2009

David J. Kappos
*Director of the United States Patent and Trademark Office*